United States Patent
Arnoni et al.

(10) Patent No.: US 12,065,683 B2
(45) Date of Patent: Aug. 20, 2024

(54) MALTOSE SYRUPS, COMESTIBLES COMPRISING THE SYRUP, AND PROCESS FOR MAKING THE SAME

(71) Applicant: Corn Products Development, Inc., Westchester, IL (US)

(72) Inventors: Laercio Arnoni, Bridgewater, NJ (US); Jose Bertoli, Bridgewater, NJ (US); Walter Yamamoto, Bridgewater, NJ (US)

(73) Assignee: Corn Products Dev elopment, Inc., Westchester, IL (US)

( * ) Notice: Subject to any disclaimer, the term of this patent is extended or adjusted under 35 U.S.C. 154(b) by 0 days.

(21) Appl. No.: 16/639,452

(22) PCT Filed: Aug. 14, 2018

(86) PCT No.: PCT/US2018/046756
§ 371 (c)(1),
(2) Date: Feb. 14, 2020

(87) PCT Pub. No.: WO2019/040327
PCT Pub. Date: Feb. 28, 2019

(65) Prior Publication Data
US 2021/0032668 A1 Feb. 4, 2021

Related U.S. Application Data

(60) Provisional application No. 62/548,126, filed on Aug. 21, 2017.

(51) Int. Cl.
*C12P 19/22* (2006.01)
*A23L 29/30* (2016.01)
(Continued)

(52) U.S. Cl.
CPC ............... *C12P 19/22* (2013.01); *A23L 29/35* (2016.08); *C12C 5/026* (2013.01); *C12P 19/12* (2013.01); *C12P 19/14* (2013.01); *C13K 7/00* (2013.01)

(58) Field of Classification Search
CPC ........... C12P 19/22; C12P 19/12; C12P 19/14; A23L 29/35; C12C 5/026; C13K 7/00
(Continued)

(56) References Cited

U.S. PATENT DOCUMENTS 4,814,267 A * 3/1989 Zeikus ................. C12N 9/2414
435/95
2011/0061645 A1 3/2011 Fosdick et al.
(Continued)

FOREIGN PATENT DOCUMENTS

EP 1980614 A2 10/2008
JP 2001086946 A * 4/2001
(Continued)

OTHER PUBLICATIONS

Translation of RU-2205209-C2 (Year: 2003).*
(Continued)

*Primary Examiner* — Brent T O'Hern
(74) *Attorney, Agent, or Firm* — Rachael Casey

(57) ABSTRACT

Disclosed herein is one or more maltose syrup having a (i) viscosity of 10,000 cP or less at 40° C. and 81.5% solids, and/or (ii) distribution of polysaccharides comprising 12% or less DP1, 42% or more DP2, 10% or more DP3, and 20.0%-33.0% DP4+, and the process for making and comestibles containing said syrup.

14 Claims, 1 Drawing Sheet

(51) Int. Cl.
*C12C 5/02* (2006.01)
*C12P 19/12* (2006.01)
*C12P 19/14* (2006.01)
*C13K 7/00* (2006.01)

(58) Field of Classification Search
USPC .......................................................... 536/123
See application file for complete search history.

(56) References Cited

U.S. PATENT DOCUMENTS

2015/0111259 A1* 4/2015 Kleinhout ............... C12P 19/12
435/99
2015/0322470 A1 11/2015 Furlan
2016/0122442 A1 5/2016 Andersen

FOREIGN PATENT DOCUMENTS

RU 2205209 C2 * 5/2003
WO WO-2016113590 A1 * 7/2016 ............... C12C 7/24

OTHER PUBLICATIONS

Translation of JP-2001086946-A (Year: 2001).*
Nebesny E: "Carbohydrate Compositions and Molecular Structure of Dextrins in Enzymatic High Maltose Syrups", Starch/Starke, Wiley-VCH Verlag, Weinheim, DE, vol. 42, No. 11, Jan. 1, 1990, pp. 437-444.
Mironescu, Influence of the Liquified Starch Composition of ph on the Saccharification of the Obtaining of Maltose Syrup. Bulletin of the University of Agricultural and Veterinary Medicine. 66. pages 364-369 (2009).

* cited by examiner

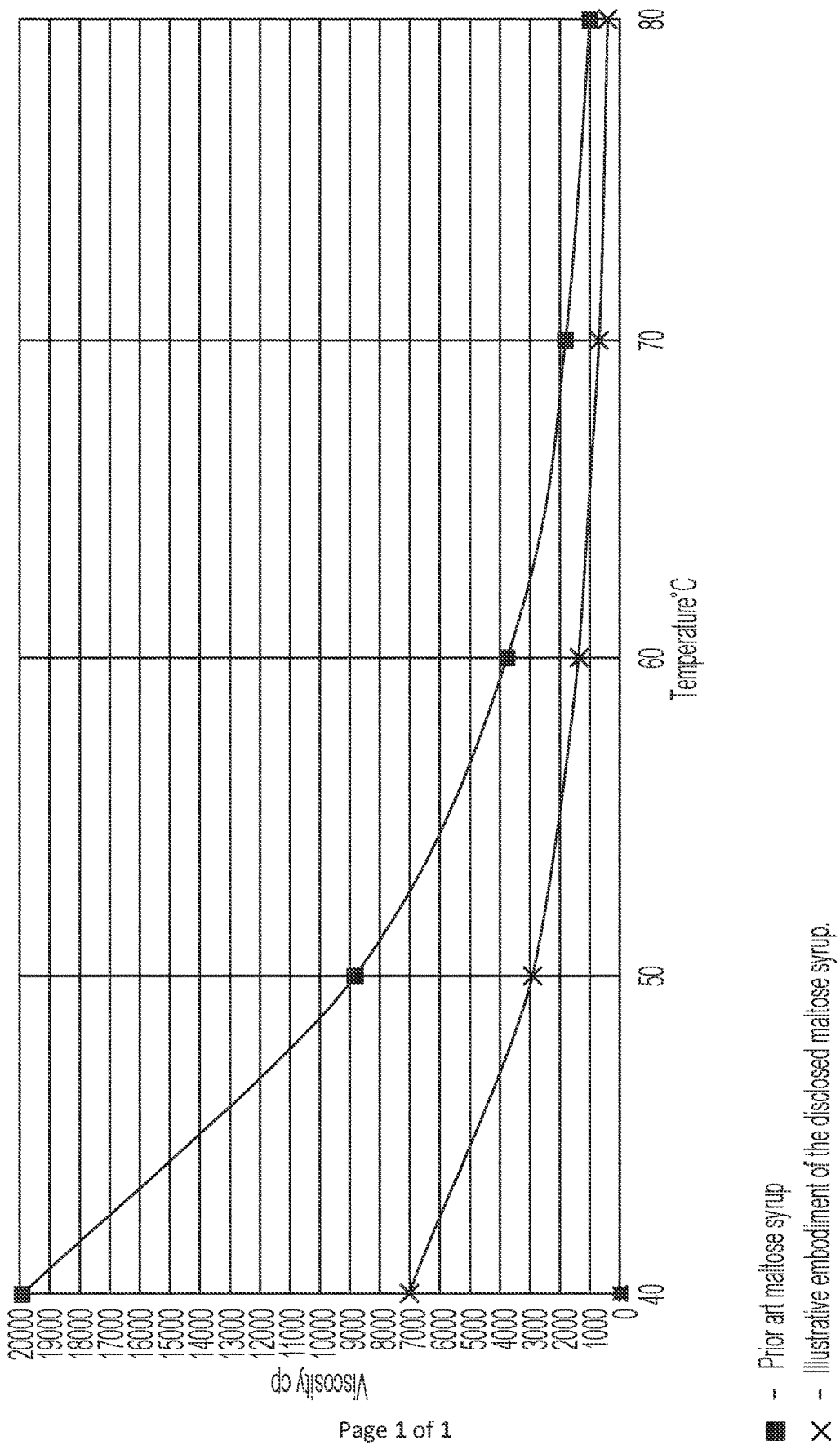

MALTOSE SYRUPS, COMESTIBLES COMPRISING THE SYRUP, AND PROCESS FOR MAKING THE SAME

CROSS-REFERENCE TO RELATED APPLICATIONS

This application is a US National Stage under 35 USC § 371 of International Application No. PCT/US2018/046756, filed Aug. 14, 2018, which claims priority to U.S. Provisional Application Ser. No. 62/548,126, filed on Aug. 21, 2017, which are is both hereby incorporated by reference herein in their entirety.

This specification discloses maltose syrups, and comestibles comprising the syrups and process for making the same. More specifically the maltose syrups comprise at least 42% maltose and have are more fluid compared to prior art maltose syrups.

Maltose syrup is an important ingredient for the brewing industry, such syrups typically have a DE between 40 and 50, and at most around 50% maltose content. More particularly, because it has lower application costs, it can be used as a substitute carbohydrate source, substituting for part of the soluble extract provided by barley malt. Prior art, maltose syrups of this type, however, have high viscosity, at 18,000 cP at 50° and 60° C. and 81.5% of solids, making them difficult to handle at such temperatures. So prior art syrups are typically handled at temperatures between 50° and 55° C., which thins the syrup, but also increases energy consumption.

In an embodiment, the maltose syrups are obtained from starch. In another embodiment the process for obtaining maltose syrup from an aqueous starch mixture comprises hydrolyzing the starch mixture during a liquefaction step to obtain a mixture comprising polysaccharides; and further hydrolyzing the mixture comprising polysaccharides during a saccharification step comprising adding a plurality of amylase enzymes and a pullulanase enzyme to the polysaccharide mixture to obtain the maltose syrup. In another embodiment the amylases are selected from the group consisting of a fungal alpha-amylase, a bacterial alpha-amylase, a maltogenic amylase, and a beta-amylase.

In an embodiment the maltose syrup has viscosity of 10,000 cP or less at 40° C. and 81.5% solids. In another embodiment the maltose syrup has a distribution of polysaccharides comprising 12% or less saccharides having a degree of polymerization ("DP") of 1, 42% or more saccharides having DP2, 10% or more saccharides having DP3, and between 20.0% and 33.0% saccharides having DP4+ (four or more linked saccharide units). In yet another embodiment the maltose syrup has a dextrose equivalent between 40 and 50.

In an embodiment the maltose syrup is used in a comestible comprising the maltose syrup and a second edible ingredient.

BRIEF DESCRIPTION OF THE FIGURE

FIG. 1 graphically compares the viscosity of a prior art maltose syrups and an illustrative embodiment of the disclosed maltose syrups.

In embodiments the process uses two hydrolysis steps to convert an aqueous starch mixture into maltose syrup. In another embodiment the process is used to make maltose syrups having a dextrose equivalent of greater than 40, or between 40 and 50. In yet another embodiment, maltose syrups have a maltose content of at least 42% and a dextrose equivalent between 40 and 50.

In an embodiment the maltose syrup is obtained from an aqueous starch mixture using starch of any suitable starch source including, for example, but not limited to starch from cereals, roots, and tubers, and more particularly from maize, cassava, potatoes, wheat, rice, sorghum, arrowroot, sago, pulses, oats, etc. The starch source also may be a low amylose and high amylose variant of the foregoing or other starches. In other embodiments the mixture may be a mixture of the foregoing starches and/or other starches.

The two hydrolysis steps are called a liquefaction step and a saccharification step. In embodiments the aqueous starch mixture is subjected to a liquefaction step that uses a suitable acid to make a mixture comprising polysaccharides. In such embodiments, the acid is any acid typically used in starch processing, for example, but not limited to sulfuric acid or hydrochloric acid. In a further embodiment the acid is added in an amount sufficient for the pH of the aqueous starch mixture to be between 1.8 and 2.2. In another embodiment acid is added to the aqueous starch mixture in the amount of from 0.01 to 0.04 meq/mL. In still another embodiment acid hydrolysis is run at temperatures ranging from 130° to 150°.

In yet another embodiment, liquefaction uses an enzyme suitable for making the mixture comprising polysaccharides. In such embodiments, the enzyme is any enzyme suitable for hydrolyzing the 1,4 glucosidic bonds. In a further embodiment, alpha-amylase is mixed with the aqueous starch mixture in the amount of from 0.05 to 0.80 g of enzyme per kg of starch on a dry basis. In yet further embodiments the reaction runs at temperatures ranging from 90° C. to 110° C. In still other embodiments the pH ranges varies from 6.0 to 7.0. In a still further embodiment, liquefaction uses an alpha-amylase that is thermostable at temperatures used to gelatinize starch (e.g. greater than 100° C., and typically between 100° C. and 160° C.). The enzymatic liquefaction step may be run once, or more than once in order to ensure that the starch is sufficiently gelatinized before it subjected to saccharification. In one embodiment the liquefaction comprises a using a single does, and single heating cycle (a "single heating/enzyme dosage liquefaction"). In another embodiment the liquefaction step uses twice the dose of enzyme added during the course heating steps (a "double heating/enzyme dosages or "DEDH"). In an embodiment the DEDH is done by running two complete liquefaction cycles sequentially. In another embodiment the DEDH adds twice the dose over enzyme over a single heating cycle, but which is run for twice the amount of time as for a single heating cycle.

In embodiments the liquefaction is run until the mixture comprising polysaccharides has a dextrose equivalent ranging from 10 to 25. In other embodiments liquefaction is stopped by any appropriate means for example adjusting the pH of the mixture comprising polysaccharides to deactivate the enzyme, or by adjusting the temperature to deactivate the enzyme. In another embodiment the alpha-amylase of the liquefaction step is not deactivate, but is used during the saccharification step. In still other embodiments the same alpha-amylase is used during both the liquefaction step and the saccharification step, but is added after the alpha amylase of the liquefaction step has been deactivated.

In embodiments the result of the liquefaction step is a composition comprising polysaccharides. The composition comprising polysaccharides is then subjected to a saccharification step. In embodiments the saccharification step comprises at least three enzymes. In another embodiment, the saccharification step comprises at least four enzymes. In still another embodiment the saccharification step use five enzymes. In even another embodiment the saccharification step comprises using a plurality of enzymes wherein at least one of the enzymes is capable of hydrolyzing 1,4 glucosidic bonds of the polysaccharides in the mixture comprising polysaccharides, and at least one of the enzymes is capable of hydrolyzing the 1,6 gludosidic bonds of the polysaccharides in the mixture comprising polysaccharides. In yet still another embodiment the at least one enzyme capable of hydrolyzing 1,4 glucosidic bonds of the polysaccharides in the mixture comprising polysaccharides is an alpha-amylase, and the at least one enzyme capable of hydrolyzing the 1,6 glucosidic bonds of the polysaccharides in the polysaccharide mixture is a pullulanase. In even still another embodiment the saccharification comprises a plurality of alpha-amylases from different sources. In yet even still another embodiment the saccharification step comprises using a plurality of enzymes selected from the group comprising a bacterial alpha-amylase, a fungal alpha-amylase, a maltogenic amylase, a pullulanse, and a beta-amylase. In a further embodiment, the saccharification step uses a bacterial alpha-amylase, a fungal alpha-amylase, a maltogenic amylase, a pullulanse, and a beta-amylase. In an even further embodiment the saccharification step comprises a plurality of alpha amylase enzymes from different sources and a pullulanase. In a still further embodiment, the fungal alpha-amylase enzyme is chosen to preferentially form maltose (DP2). In an even further embodiment the maltogenic amylase enzyme is chosen to preferentially to digest maltotriose to form DP2 saccharides. In a yet further embodiment the beta-amylase is selected to preferentially form DP2 saccharides from the non-reducing ends of the polysaccharide chains. In a yet still further embodiment the bacterial alpha-amylase is selected to randomly digest 1,4 glucosidic linkages within the polysaccharide mixture. In an even still further embodiments a fungal alpha-amylase enzyme is used in amount of between 0.28 to 0.52 g enzyme per kg of starch (dry basis). In a yet even further embodiment a bacterial alpha-amylase enzyme is used in the amount of between 0.20 to 2.10 g enzyme per kg of starch (dry basis). In a yet even still further embodiment the pullulanase enzyme is used in an amount of between 0.20 to 0.27 g enzyme per kg starch (dry basis). In an additional embodiment a maltogenic amylase enzyme is used in amount of between 0.90 to 1.30 g enzyme per kg of starch (dry basis). In a still additional embodiment a beta-amylase is used in amount of between 0.20 to 0.24 g enzyme per kg starch (dry basis). In yet still an additional embodiment the saccharification step uses a bacterial alpha-amylase, a fungal alpha-amylase, a pullulanse, optionally a maltogenic amylase, and optionally a beta-amylase.

In embodiments the saccharification step is run until the desired DP2 content is achieved. In another embodiment the temperature of the polysaccharide mixture during the saccharification step is between 40° and 85° C. In still another embodiment the pH of polysaccharide mixture during the saccharification step is between 4.0 to 7.5. In yet another embodiment the saccharification step runs for at least 6 hours, or between 6 and 12 hours.

In an embodiment the fungal alpha amylase, bacterial alpha-amylase, beta-amylase, pullulanase, and maltogenic amylase are commercially available. In another embodiment, the commercially available bacterial alpha-amylases include, for example, but are not limited to Termamyl 120L, BAN 480L, Liquozyme Supra, Spezyme Fred. In yet another embodiment commercially available pullulanases include, for example, but are not limited to Promozyme D2, Optimax L 1000, Promozyme 400. In still another embodiment commercially available fungal alpha-amylase enzymes include, for example, but are not limited to Fungamyl 800L, Clarase L. In even another embodiment commercially available maltogenic amylase enzymes include, for example, but are not limited to Maltogenase L. In yet still another embodiment commercially available beta-amylase enzymes include, for example, but are not limited to Spezyme DBA, Spezyme BBA.

In embodiments the maltose syrups made from the above disclosed processes have DP1, DP2, DP3, and DP4+ saccharide amounts that are similar to prior art maltose syrups. In an embodiment, the maltose syrup has a DP profile comprising a maximum content of DP1 saccharides of less than 12%, or between 0% and 12%, and minimum content of DP2 saccharides of at least 40%, at least 42% or between 40% and 70%, or between 40% and 50%, or between 42% and 50% and a minimum content of DP3 saccharides of at least 10%, or between 10% and 38%, and a minimum content of DP4+ saccharides (saccharide polymers of at least four units) of between 20% to 33% but with a DP4+. In another embodiment the distribution of DP4+ saccharides have a lower number average molecular weight than prior art maltose syrups, or have on average a lower DP than prior art maltose syrups, or have a lower weight average molecular weight than prior art maltose syrups.

Without being bound by theory it is believed that the difference in the distribution of DP4+ saccharides, in terms of molecular weight and/or degree of polymerization, results in the observed lower viscosity for maltose syrups made by the disclosed process compared with the maltose syrups of the prior art. In embodiments maltose syrups have a viscosity of less than about 10,000 cP. In another embodiment maltose syrups have a viscosity of between 1,000 and 10,000 cP. In yet another embodiment, a maltose syrup having a solids content of at least 75%, or at least 80%, or at least 81%, or about 81.5% or between 75% and 85% has a viscosity of between 1,000 and 10,000 cP. In still another embodiment the maltose syrups have a viscosity of less than 10,000 cP, between 10,000 and 1,000 cP, or between 10,000 and 7,000 cP at 45° C. or less, or at 40° C. or less, or at between 35° and 45° C. In even another embodiment the maltose syrups having 81.5% solids content (w/w) have a viscosity of less than 10,000 cP at 40° C. or less than 3,500 cP at 50° C., or less than 1,500 cP at 60° C., or less than 1,000 cP at 70° C., or less than 500 cP at 80° C.

Within in this specification polysaccharides refer generally to the mixture of glucose molecules and glucose polymers derived from starch hydrolysis by the disclosed processes. Accordingly, polysaccharides include starch derivatives having a degree of polymerization of 1 (DP1)—i.e. glucose—through DPn; more specifically, the term polysaccharide is used as a short hand to refer to a collection of molecules that may be more accurately described as including glucose, maltose, dextrin, maltodextrins, and/or oligosaccharides.

In embodiments the maltose syrups are used to make comestibles. In another embodiment the comestible is a food product. In yet another embodiment the comestible is a beverage. In even another embodiment the comestible is fermented. In still another embodiment the comestible is fermented and comprises ethanol. In yet still another embodiment the comestible is a beer or fermented malt beverage. In yet even another embodiment the comestible comprises a maltose syrup and another edible ingredient. In still even another embodiment the other edible ingredient is any edible ingredient including, for example, but not limited to liquids (including, for example, but not limited to water, liquid dairy products, fruit and/or vegetable juice, honey, extracts, syrups, and other liquefied flavorings) sweeteners (including, for example, but not limited to sucrose, allulose, fructooligosaccharides, rebaudiosides (e.g. rebaudioside A, or rebaudioside M), other zero or reduced calorie sweeteners), dextrin, maltodextrins lecithin, malts (malted barley, etc.), oils and other liquefied fats, emulsifiers, eggs (including in powdered form), starches and flours (including, for example, but not limited to wheat, corn, cassava, potato, sago, sorghum, arrowroot, oat, rice, pulses, and low amylose or high amylose variants those starches, and others, and unmodified and modified variants those starches and others) yeast, bacteria, fruit, salts, seasonings, gums, proteins (including, for example, but not limited to protein concentrates and protein isolates whether from plants, grains, pulses, dairy products, etc.).

In embodiments the maltose syrups are substituted for at least some of the barley malt in a process for making a fermented comestible. In another embodiment the process is for making a fermented beverage. In another embodiment the process is for making a beer or other fermented malt beverage. In other embodiments the process of making the comestible comprises mixing the maltose syrup with another edible ingredient. In still even another embodiment the other edible ingredient is any edible ingredient including, for example, but not limited to liquids (including, for example, but not limited to water, liquid dairy products, fruit and/or vegetable juice, honey, extracts, syrups, and other liquefied flavorings) sweeteners (including, for example, but not limited to sucrose, allulose, fructooligosaccharides, rebaudiosides (e.g. rebaudioside A, or rebaudioside M), other zero or reduced calorie sweeteners), dextrin, maltodextrins lecithin, malts (malted barley, etc.), oils and other liquefied fats, emulsifiers, eggs (including in powdered form), starches and flours (including, for example, by not limited to wheat, corn, cassava, potato, sago, sorghum, arrowroot, oat, rice, pulses, and low amylose or high amylose variants those starches, and others, and unmodified and modified variants those starches and others) yeast, bacteria, fruit, salts, seasonings, gums, proteins (including, for example, but not limited to protein concentrates and protein isolates whether from plants, grains, pulses, dairy products, etc.).

Recitation of a specific range includes recitation of all sub ranges within the specified broader range.

The maltose syrups disclosed in this specification are further described by way of the examples below. The examples are illustrative and are not intended to be limiting in any way. Persons of ordinary skill in the art will understand that the parameters of the processes described above may be varied yet still be within the spirit of the invention and the scope of the claims.

Table 1 below shows the comparative result between the viscosities presented by a prior art maltose syrup and an illustrative embodiment of the disclose maltose syrup. Table 1 reports the viscosity of syrups having a solids content of 81.5%. The same results are also shown in FIG. 1.

TABLE 1

| | Viscosity RVA (cP) | |
|---|---|---|
| Temperature | Prior art maltose syrup | Illustrative low viscosity maltose syrup |
| 40° C. | 19,900 | 7,000 |
| 50° C. | 8,800 | 2,900 |
| 60° C. | 3,800 | 1,300 |
| 70° C. | 1,800 | 700 |
| 80° C. | 900 | 400 |

The invention claimed is:

1. A maltose syrup comprising between 42% and 50% (w/w) maltose and having a viscosity of between 1,000 and 10,000 cP at between 35° and 45° C. made by a process comprising hydrolyzing an aqueous starch mixture during a liquefaction step to obtain a mixture comprising polysaccharides; and hydrolyzing the mixture comprising polysaccharides during a saccharification step comprising adding to the mixture comprising polysaccharides a plurality of amylase enzymes, and a pullulanase enzyme to obtain the maltose syrup.

2. The maltose syrup of claim 1, wherein the maltose syrup is 81.5% (w/w) solid.

3. The maltose syrup of claim 1 further having a distribution of saccharides comprising 0%-12% saccharides having a Degree of Polymerization ("DP") of 1, 42% or more saccharides having DP2, 10% or more saccharides having DP-3, and between 20.0% and 33.0% saccharides having DP4+.

4. The maltose syrup of claim 1 further having a dextrose equivalent between 40 and 50.

5. A comestible comprising a first edible ingredient comprising the maltose syrup of claim 1 and a second edible ingredient.

6. The comestible of claim 5, wherein the comestible is selected from a beverage, a fermented beverage, a beer, or other fermented malt beverage.

7. The comestible of claim 5, wherein the comestible is fermented.

8. The comestible of claim 5 further comprising ethanol or a malted ingredient.

9. A method of making a comestible comprising mixing a first edible ingredient comprising the maltose syrup of claim 1 and a second edible ingredient.

10. The maltose syrup of claim 1, wherein the maltose syrup is 81.5% (w/w) solid.

11. The maltose syrup of claim 1 further comprising a distribution of saccharides comprising 0%-12% saccharides having a Degree of Polymerization ("DP") of 1, 42% or more saccharides having DP2, 10% or more saccharides having DP-3, and between 20.0% and 33.0% saccharides having DP4+.

12. The maltose syrup of claim 1 further comprising a dextrose equivalent between 40 and 50.

13. A comestible comprising a first edible ingredient comprising the maltose syrup of claim 1 and a second edible ingredient.

14. A method of making a comestible comprising mixing a first edible ingredient comprising the maltose syrup of claim 1 and a second edible ingredient.

* * * * *